(12) United States Patent
Cookson et al.

(10) Patent No.: US 10,011,603 B2
(45) Date of Patent: Jul. 3, 2018

(54) PROCESS FOR PREPARING A CARBAPENEM ANTIBIOTIC

(71) Applicant: JOHNSON MATTHEY PUBLIC LIMITED COMPANY, London (GB)

(72) Inventors: James Cookson, Reading (GB); Robert John McNair, West Depford, NJ (US); Deepak Vasant Satoskar, Maharashtra (IN)

(73) Assignee: Johnson Matthey Public Limited Company, London, England (GB)

(*) Notice: Subject to any disclaimer, the term of this patent is extended or adjusted under 35 U.S.C. 154(b) by 0 days.

(21) Appl. No.: 15/129,210

(22) PCT Filed: Mar. 26, 2015

(86) PCT No.: PCT/GB2015/050917
§ 371 (c)(1),
(2) Date: Sep. 26, 2016

(87) PCT Pub. No.: WO2015/145161
PCT Pub. Date: Oct. 1, 2015

(65) Prior Publication Data
US 2017/0210744 A1    Jul. 27, 2017

Related U.S. Application Data

(60) Provisional application No. 61/971,041, filed on Mar. 27, 2014.

(51) Int. Cl.
*C07D 477/08* (2006.01)
(52) U.S. Cl.
CPC ................ *C07D 477/08* (2013.01)

(58) Field of Classification Search
None
See application file for complete search history.

(56) References Cited

U.S. PATENT DOCUMENTS 4,888,344 A    12/1989   Sunagawa et al.

FOREIGN PATENT DOCUMENTS

| EP | 1 426 376 A1 | 6/2004 |
|---|---|---|
| EP | 2 141 167 A1 | 1/2010 |
| EP | 2 388 261 A2 | 11/2011 |
| EP | 2388261 | 11/2011 |
| WO | 2011/160020 A2 | 12/2011 |
| WO | 2011160020 | 12/2011 |
| WO | 2012/038979 A2 | 3/2012 |
| WO | 2012139414 | 10/2012 |

OTHER PUBLICATIONS

Tewari et al., "An Improved Procedure for Preparation of Carbapenem Antibiotic: Meropenem", Organic Process Research & Development, 2007, vol. 11 No. 4, pp. 773-775.
Acres et al., "The Design and Preparation of Supported Catalysts", Catalysis, vol. 4, Jan. 1981, Royal Society of Chemistry, pp. 1-30.
United Kingdom Combined Search and Examination Report under Sections 17 and 18(3) dated Dec. 24, 2015; Application No. GB1505210.3.
International Search Report, dated Jun. 19, 2015, from corresponding PCT Application.

*Primary Examiner* — Deepak R Rao
*Assistant Examiner* — Laura M Daniel
(74) *Attorney, Agent, or Firm* — Baker & Hostetler LLP

(57) ABSTRACT

A process for the preparation of a carbapenem, includes the step of treating a solution of a protected carbapenem with hydrogen gas in the presence of a heterogeneous catalyst to form the carbapenem, wherein the heterogeneous catalyst includes at least two platinum group metals.

15 Claims, 5 Drawing Sheets

| Catalyst Description | Carbon Support* | Weight % Pd metal | Weight % Pt metal | Conversion by HPLC (%) | Isolated Meropenem Mole Yield (%) | HPLC Purity of Isolated Meropenem (%) |
|---|---|---|---|---|---|---|
| 4% Pd,1% Pt/C | A | 4.0 | 1.0 | 100 | 85 | 99.70 |
| 4% Pd,1% Pt/C | B | 4.0 | 1.0 | 100 | 83 | 99.88 |
| 4% Pd,1% Pt/C | C | 4.0 | 1.0 | 100 | 79 | 99.47 |
| 4.5%Pd,0.5%Pt/C | A | 4.5 | 0.5 | 100 | 79 | 99.81 |
| 4.5%Pd,0.5%Pt/C | B | 4.5 | 0.5 | 100 | 79 | 99.44 |
| 4.5%Pd,0.5%Pt/C | C | 4.5 | 0.5 | 100 | 79 | 99.85 |
| 4.9%Pd,0.1%Pt/C | A | 4.9 | 0.1 | 100 | 84 | 99.87 |
| 4.9%Pd,0.1%Pt/C | B | 4.9 | 0.1 | 100 | 82 | 99.87 |
| 4.9%Pd,0.1%Pt/C | C | 4.9 | 0.1 | 100 | 70 | 99.81 |

* A = Ceca L4S; B = Ceca ENO; C = Ceca CPL

FIGURE 2

| Catalyst Description | Carbon Support* | Weight % Pd Metal | Weight % Pt Metal | Conversion by HPLC (%) | Isolated Meropenem Mole Yield (%) | HPLC Purity of Isolated Meropenem (%) |
|---|---|---|---|---|---|---|
| 10% Pd/C ** | A | 10.0 | 0 | 100 | 77 | 99.5 |
| 9.9% Pd, 0.1% Pt/C | A | 9.9 | 0.1 | 100 | 81 | 99.7 |
| 9.8% Pd, 0.2% Pt/C | A | 9.8 | 0.2 | 100 | 83 | 99.7 |
| 9% Pd, 1% Pt/C | A | 9.0 | 1 | 100 | 80 | 99.7 |

* A = Ceca L4S; ** not according to the invention

FIGURE 3

| Catalyst Description | Carbon Support* | Weight % Pd Metal | Weight % Pt Metal | Conversion by HPLC (%) | Isolated Meropenem Mole Yield (%) | HPLC Purity of Isolated Meropenem (%) |
|---|---|---|---|---|---|---|
| 10% Pd/C ** | B | 10.0 | 0 | 100 | 74 | 99.6 |
| 9.9% Pd, 0.1% Pt/C | B | 9.9 | 0.1 | 100 | 81 | 99.5 |
| 9.8% Pd, 0.2% Pt/C | B | 9.8 | 0.2 | 100 | 82 | 99.6 |
| 9% Pd, 1% Pt/C | B | 9.0 | 1 | 100 | 81 | 99.6 |

* B = Ceca ENO; ** not according to the invention

FIGURE 4

PROCESS FOR PREPARING A CARBAPENEM ANTIBIOTIC

The present invention is concerned with an improved process of preparing a carbapenem.

BACKGROUND

N. Tewari et al (Organic Process Research & Development 2007, 11, 773-775) describes the synthesis of meropenem from intermediates 2 and 3 without the isolation of intermediate 4. The catalyst used for the conversion of intermediate 4 to meropenem 1 is 5% Pd/C.

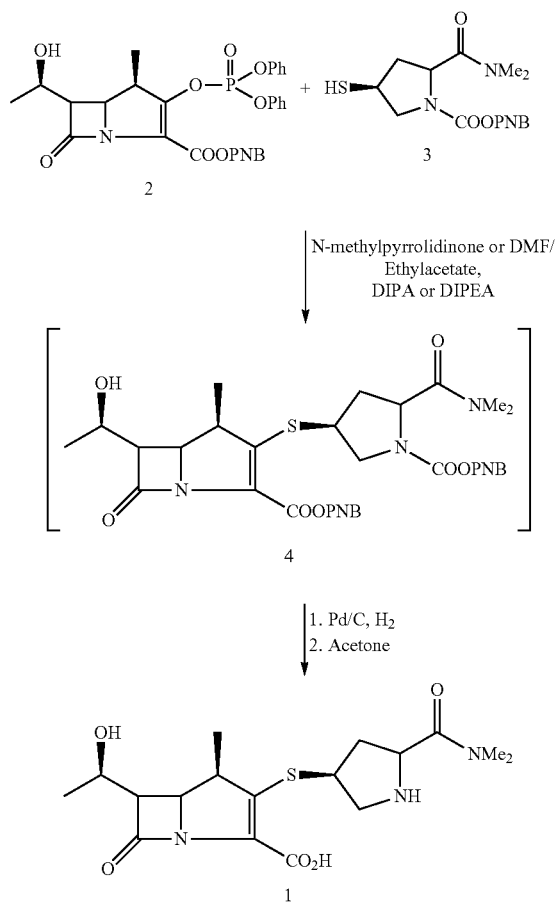

Carbapenem precursors and carbapenem products can be problematic to work with in hydrogenation reactions using Pd/C or Pt/C catalysts as the sulfur-containing side chain may act as a catalyst poison. Alternatively or in addition, the carbapenem products may be unstable. Accordingly, there remains a need to provide an improved process for the preparation of carbapenems, such as meropenem.

There remains a need to provide a process for the preparation of a carbapenemcarbapenem which overcomes the limitations in the prior art.

SUMMARY OF THE INVENTION

In one aspect, the present invention provides a process for the preparation of a carbapenem, said process comprising the step of treating a solution of a protected carbapenem with hydrogen gas in the presence of a heterogeneous catalyst to form the carbapenem, wherein the heterogeneous catalyst comprises at least two platinum group metals.

In another aspect, the invention provides a use of a heterogeneous catalyst in the preparation of a carbapenem, comprising the treatment of a solution of a protected carbapenem with hydrogen gas in the presence of a heterogeneous catalyst to form the carbapenem, wherein the heterogeneous catalyst comprises at least two platinum group metals.

DEFINITIONS

The point of attachment of a moiety or substituent is represented by "—". For example, —OH is attached through the oxygen atom.

"Alkyl" refers to a straight-chain, branched or cyclic saturated hydrocarbon group. In certain embodiments, the alkyl group may have from 1-20 carbon atoms, in certain embodiments from 1-15 carbon atoms, in certain embodiments, 1-8 carbon atoms. The alkyl group may be unsubstituted. Alternatively, the alkyl group may be substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, cyclopropyl, n-butyl, iso-butyl, sec-butyl, tert-butyl, cyclobutyl, n-pentyl, cyclopentyl, n-hexyl, cyclohexyl and the like.

"Aryl" or "Ar" refers to an aromatic carbocyclic group. The aryl group may have a single ring or multiple condensed rings. In certain embodiments, the aryl group can have from 5-20 carbon atoms, in certain embodiments from 6-15 carbon atoms, in certain embodiments, 6-12 carbon atoms. The aryl group may be unsubstituted. Alternatively, the aryl group may be substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Arylalkyl" refers to an optionally substituted group of the formula aryl-alkyl-, where aryl and alkyl are as defined above.

"Substituted" refers to a group in which one or more (e.g. 1, 2, 3, 4 or 5) hydrogen atoms are each independently replaced with substituents which may be the same or different. Examples of substituents include but are not limited to -halo, —C(halo)$_3$, —R$^a$, =O, —O—R$^a$, —S—R$^a$, —NR$^a$R$^b$, —CN, —SCN, —NCS, —NO$_2$, —C(O)—R$^a$, —COOR$^a$, and —CONR$^a$R$^b$, such as -halo, —C(halo)$_3$, —R$^a$, —O—R$^a$ and —NO$_2$. R$^a$ and R$^b$ are independently selected from the groups consisting of H, alkyl, aryl, arylalkyl. R$^a$ and R$^b$ may be unsubstituted or further substituted as defined herein.

DETAILED DESCRIPTION

Carbapenems are a class of β-lactam antibiotics which typically have a broad spectrum of antibacterial activity. Carbapenems can be represented by the following general structural formula:

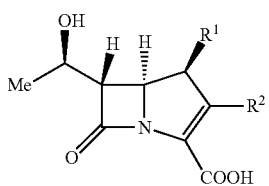

$R^1$ may be —H or —Me. $R^2$ is a functionalised side chain, which comprises a sulfur-containing moiety. Examples of carbapenems include thienamycin, imipenem, panipenem, meropenem, ertapenem, bipenem or the like.

The present inventors have found that the synthesis of carbapenems is improved if a heterogeneous catalyst comprising at least two platinum group metals (PGMs) is used in place of heterogeneous catalysts containing a single PGM. Accordingly, as mentioned above, the present invention provides a process for the preparation of a carbapenem, said process comprising the step of treating a solution of a protected carbapenem with hydrogen gas in the presence of a heterogeneous catalyst to form the unprotected carbapenem, wherein the heterogeneous catalyst comprises at least two platinum group metals.

The protected carbapenem contains protecting groups which were introduced at an earlier stage of the synthesis and which are removable in hydrogenolysis reactions. Hydrogenolysis is a chemical reaction whereby a C—N single bond and/or a C—O single bond are cleaved (i.e. undergoes "lysis") when treated with hydrogen gas in the presence of a heterogeneous catalyst.

The protected carbapenem may comprise one or more protecting groups selected from the group consisting of unsubstituted benzyl, substituted benzyl, unsubstituted-carboxybenzyl, substituted-carboxybenzyl groups, and a combination thereof.

As is known in the art, a benzyl group is a protecting group used in organic synthesis for the protection of e.g. carboxylic acids. A benzyl group has the general structure —CH$_2$-phenyl, wherein the phenyl group may be unsubstituted or substituted. A benzylation reaction, therefore, is a chemical reaction in which a benzyl group is introduced into a molecule (i.e. the molecule has been benzylated). A molecule may be benzylated by methods known in the art. Conversely, a debenzylation reaction is a chemical reaction in which a benzyl group is removed from a molecule (i.e. the molecule has been debenzylated).

The protected carbapenem may contain one or more benzyl groups, although typically no more than two. In one embodiment, therefore, the carbapenem comprises one benzyl group. In other embodiment, the carbapenem comprises two benzyl groups.

A carboxybenzyl group is a protecting group used in organic synthesis for protection of e.g. amines. A carboxybenzyl group has the general structure —C(O)—O—CH$_2$-phenyl, wherein the phenyl group may be unsubstituted or substituted. A carboxybenzylation reaction, therefore, is a chemical reaction in which a carboxybenzyl group is introduced into a molecule (i.e. the molecule has been carboxybenzylated). A molecule may be carboxybenzylated by methods known in the art. Conversely, a decarboxybenzylation reaction is a chemical reaction in which a carboxybenzyl group is removed from a molecule (i.e. the molecule has been decarboxybenzylated).

The protected carbapenem may contain one or more carboxybenzyl groups, although typically no more than two. In one embodiment, therefore, the protected carbapenem comprises one carboxybenzyl group. In other embodiment, the protected carbapenem comprises two carboxybenzyl groups.

In certain embodiments, the protected carbapenem may comprise a benzyl group and a carboxybenzyl group.

The protected carbapenem is treated to form the carbapenem, wherein the protected carbapenem and carbapenem products are selected from the group consisting of:

| Protected Carbapenem | Carbapenem |
|---|---|
| Protected Meropenem | Meropenem |
| Protected Imipenem | Imipenem |
| Protected Ertapenem | Ertapenem |
| Protected Thienamycin | Thienamycin |
| Protected Panipenem | Panipenem |
| Protected Doripenem | Doripenem |

Each of the protected carbapenems listed above may comprise a benzyl group and a carboxybenzyl group. In one preferred embodiment, when the protected carbapenem is protected meropenem, the protected meropenem may comprise a benzyl group and a carboxybenzyl group.

Examples of suitable benzyl groups include but are not limited to —CH$_2$C$_6$H$_5$ and —CH$_2$—C$_6$H$_4$—NO$_2$, wherein the —NO$_2$ group may be ortho-, meta- or para-, preferably para-. In one embodiment, the benzyl group is —CH$_2$C$_6$H$_5$. In another embodiment, the benzyl group is —CH$_2$C$_6$H$_4$—NO$_2$.

Examples of suitable carboxybenzyl groups include but are not limited to:

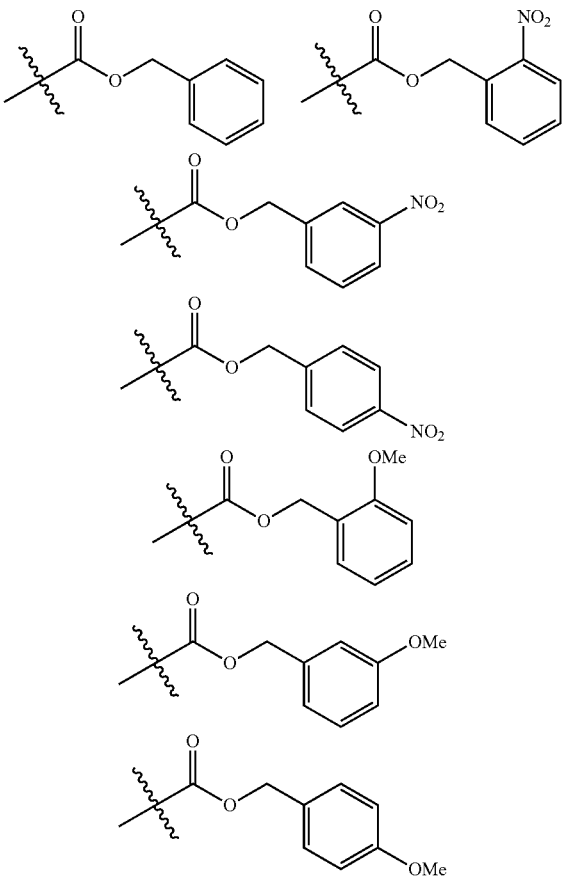

In one embodiment, the carboxybenzyl group is

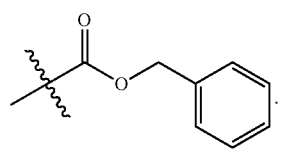 [SMILES: *C(=O)OCc1ccccc1]

In another embodiment, the carboxybenzyl group is

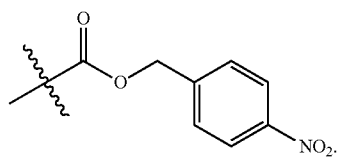 [SMILES: *C(=O)OCc1ccc([N+](=O)[O-])cc1]

In one embodiment, the protected carbapenem is protected meropenem, wherein the protected meropenem comprises a —CH$_2$C$_6$H$_4$—NO$_2$ and a

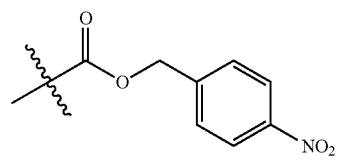 [SMILES: *C(=O)OCc1ccc([N+](=O)[O-])cc1]

group. In one preferred embodiment, the protected meropenem is the compound of formula 1.

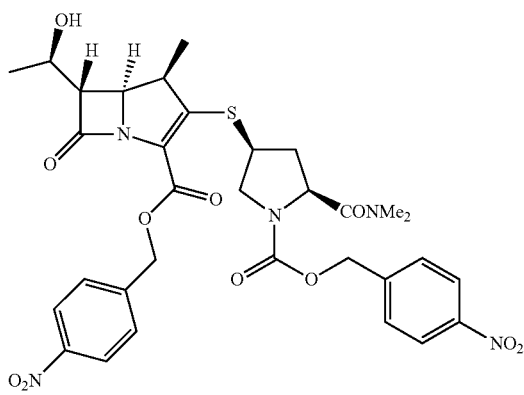

The protected carbapenem may comprise water. Alternatively, the protected carbapenem may be substantially dry i.e. may comprise substantially no water. Irrespective or not of whether the protected carbapenem comprises water, the quantity of protected carbapenem used etc. is calculated on the basis of % dry weight of the protected carbapenem.

The protected carbapenem is dissolved in a suitable solvent or solvent mixture to form a solution. The solvent or solvents may be selected from the group consisting of water, protic solvents, aprotic solvents or a mixture thereof. When water is used, the quantity of water present in the catalyst and/or protected carbapenem (both of which may be used wet) may be taken into account when calculating the total quantity of water to be used. When solvent mixtures are utilised, it is generally desirable that the solvents are substantially miscible. Polar solvents include but are not limited to alcohols, such as methanol, ethanol, propanol (n- and i-), butanaol (n-, i- or t-), pentanols, hexanols. Aprotic solvents include but are not limited to ether solvents, such as tetrahydrofuran (THF) or 2-methyltetrahydrofuran (2-MeTHF), ester solvents, such as ethyl acetate or methyl acetate, chlorinated solvents, such as dichloromethane or amide solvents, such as dimethylformamide (DMF) or dimethylacetamide (DMA). In one embodiment, a solvent mixture may be utilised comprising water and THF. In other embodiment, the solvent may be ethyl acetate.

The treatment of the solution of the protected carbapenem with hydrogen gas in the presence of a heterogeneous catalyst may further comprise a base. In certain embodiments, a buffer comprising a base may be utilised. The base may be an inorganic or organic base. In one embodiment, the base can be an organic base selected from the group consisting of lutidine (e.g. 2,6-lutidine), methylmorpholine (e.g. 4-methylmorpholine), triethylamine, pyridine, (N,N-dimethylamino)pyridine (e.g. 2-(N,N-dimethylamino)pyridine, 3-(N,N-dimethylamino)pyridine or 4-(N,N-dimethylamino)pyridine), (N,N-diethylamino)pyridine (e.g. 2-(N,N-diethylamino)pyridine, 3-(N,N-diethylamino)pyridine or 4-(N,N-diethylamino)pyridine) and the like. In one preferred embodiment, the organic base is lutidine. In another embodiment, the base may be an inorganic base selected from the group consisting of hydroxides, alkoxides, carbonates or acetates. Suitable hydroxides include alkali metal hydroxides (e.g. lithium hydroxide, sodium hydroxide or potassium hydroxide) or tetraalkylammonium hydroxides (e.g. tetrabutylammonium hydroxide). Suitable alkoxides include alkali metal alkoxides (e.g. lithium alkoxide, sodium alkoxide or potassium alkoxide) or tetraalkylammonium alkoxides. Suitable carbonates include alkali metal carbonates (e.g. lithium carbonate, sodium carbonate or potassium carbonate). Suitable acetates include alkali metal acetates (e.g. lithium acetates, sodium acetates or potassium acetates).

The heterogeneous catalyst comprises at least two platinum group metals, such as two, three or four PGMs, for example two PGMs. The platinum group metals may be ruthenium, rhodium, palladium, iridium or platinum, for example, palladium and platinum. Without wishing to be bound by theory, it is believed that the two or more PGMs synergistically affect the claimed reaction and result in an enhanced conversion (i.e. amount of starting material used up in the reaction) and/or selectivity (i.e. amount of desired product formed over all products formed in the reaction).

Carbapenem precursors and carbapenem products can be problematic to work with in hydrogenation reactions using Pd/C or Pt/C catalysts as the sulfur-containing side chain may act as a catalyst poison. Without wishing to be bound by theory, it is believed that the heterogeneous catalyst comprising at least two PGMs mitigates the tendency of the carbapenem precursors, carbapenem products, sulfur-containing reaction intermediates and/or sulfur-containing reaction by-products to act as catalyst poisons.

The carbapenem product, such as meropenem, may have the propensity to degrade in the reaction mixture over time. Without wishing to be bound by theory, it is believed that the prior art heterogeneous catalysts comprising a single PGM, such as Pd/C or Pt/C, may be responsible, at least in part, for the degradation. The use of a heterogeneous catalyst comprising at least two PGMs per the present invention appears to ameliorate the carbapenem product's propensity to degrade and, as such, an increase in the yield of the carbapenem product may be obtained as compared to the prior art processes.

When the heterogeneous catalyst comprises two PGMs, the wt % ratio of one PGM to the other PGM may be in the range of about 20:about 0.001 to about 0.001:about 20, such as about 10:about 0.01 to about 0.01:about 10, for example about 5:about 0.1 to about 0.1:about 5.

When the heterogenous catalyst comprises platinum and another PGM (e.g. palladium), the wt % ratio of platinum to the other PGM may be in the range of about 0.01:about 20 to about 5.0:about 20, such as about 0.05:about 10 to about 3.75:about 10, such as about 0.1:about 5 to about 2.5:about 5.

The heterogeneous catalyst may be an alloy of two or more PGMs, such as colloidal PGM alloys, PGM alloy sponge, PGM alloy plate or PGM alloy wire. Examples of PGM alloy catalysts include but are not limited to colloidal platinum/palladium, platinum/palladium sponge, platinum/palladium plate or platinum/palladium wire.

The heterogeneous catalyst may comprise at least two platinum group metals on a solid support. The support may be selected from the group consisting of carbon, alumina, calcium carbonate, barium carbonate, barium sulfate, titania, silica, zirconia, ceria and a combination thereof. When the support is alumina, the alumina may be in the form of alpha-$Al_2O_3$, beta-$Al_2O_3$, gamma-$Al_2O_3$, delta-$Al_2O_3$, theta-$Al_2O_3$ or a combination thereof. When the support is carbon, the carbon may be in the form of activated carbon (e.g. neutral, basic or acidic activated carbon), carbon black or graphite (e.g. natural or synthetic graphite). Examples of suitable carbon supports include but are not limited to Ceca L4S, Ceca ENO and Ceca CPL.

When the heterogeneous catalyst comprises at least two platinum group metals on a solid support, the mean particle size of the heterogeneous catalysts may be in the range of about 10 to about 100 μm, such as about 15 to about 45 μm, for example about 20 to about 40 μm, such as about 23 to about 32 μm.

The total % metal dispersion on the solid support may be calculated using a metal surface area value. Total metal dispersions on the metal catalysts may range from about 0.1 to about 100%, such as about 5 to about 95%, such as about 10 to about 90%, such as about 20 to 88%, such as about 30 to about 87%, such as about 40 to about 85%. In one embodiment, the total metal dispersion for 5% total metal catalysts may range from about 40 to about 90%, such as about 50 to about 85%, such as about 53 to about 83%, such as about 56 to about 79%. In another embodiment, the total metal dispersion for 10% total metal catalysts may range from about 20 to about 80%, such as about 30 to about 70%, such as about 40 to about 68%, such as about 43 to about 64%.

The heterogeneous catalyst may comprise water. Alternatively, the heterogeneous catalyst may be substantially dry i.e. may comprise substantially no water. Irrespective or not of whether the heterogeneous catalyst comprises water, the catalyst loading etc. is calculated on the basis of % dry weight of the catalyst.

Regardless of the form of the heterogeneous catalyst, the present invention does not encompass an admixture of one individual PGM in combination with one or more other PGMs e.g. Pd/C in combination with Pt/C. Instead, the advantageous effects of the present invention occur as a result of a synergistic interaction between the two or more PGMs which have been prepared as an alloy or deposited onto the same support (e.g. Pd,Pt/C). In other words, the heterogeneous catalyst of the invention is a mixed metal catalyst.

The catalyst loading may be up to about 100 weight % of dry weight of catalyst:dry weight of protected carbapenem. In one embodiment, the catalyst loading may be up to about 50 weight %, such as up to 30 weight % and, in another embodiment, may be in the range of about 0.1-30.0 weight %. In one preferred embodiment, the catalyst loading may be about 25% by weight with respect to the substrate.

While it is typically sufficient for a single charge of hydrogenation catalyst to be added to the reaction mixture, it is envisaged that a second or further charge could be added and the hydrogenation continued if it has been determined (e.g. via in-process analysis) that the reaction has not gone to completion and starting material remains.

The concentration of the protected carbapenem in the solvent may be any suitable concentration. The concentration of the protected carbapenem:solvent may be in the range of about 0.0001:about 10 g/mL, such as about 0.001:about 1 g/mL, such as about 0.05:about 0.5 g/mL, such as about 0.01:about 0.1 g/mL, for example, 0.02 g/mL or 0.03 g/mL.

There is no particular limitation on the pressure at which the hydrogenation is carried out. In this regard, the hydrogenation may conveniently be carried out with an initial hydrogen pressure in the range of about 5 to about 500 psi, such as about 10 to about 400 psi, such as about 40 psi to about 300 psi, such as about 75 to about 290 psi, such as about 90 to about 270 psi for example, about 94 psi, 150 psi or about 260 psi.

The process of the invention may be carried out at one or more temperatures in the range of about −10° C. to about 50° C., for example about 10° C. to about 45° C., such as about 20° C. to about 40° C. It is preferred that the temperature is maintained below the decomposition temperature of the protected carbapenem and/or the carbapenem product. As such, when the protected carbapenem and/or the carbapenem product are known decompose within the temperature ranges given above, the temperature should be maintained below the decomposition temperature.

The reaction may be carried out for a period of from about several minutes to about 24 hours but is usually complete within about 2 hours for a laboratory scale reaction. On completion, the hydrogen pressure is released and the heterogeneous catalyst is separated from the reaction mixture by any appropriate method, for example, the catalyst may be filtered over Celite and optionally washed (e.g with water).

The process according to the invention may further comprise precipitating the carbapenem product from the obtained filtrate, typically by suitable cooling of the filtrate, addition of an anti-solvent, such as acetone, filtering and washing the precipitate. The resulting precipitated product may then be dried under vacuum if desired.

Suitably, the process according to the present invention may further comprise a purification step, such as a recrystallization. In this instance, the carbapenem can be dissolved in a suitable solvent or solvent mixture (such as those described above), followed by suitable heating, filtration and addition of an anti-solvent, such as acetone.

Typically, the process can employ HPLC analysis, to ensure that an appropriate carbapenem quality is obtained. Suitable HPLC conditions are described below in the accompanying Examples.

In another aspect, the present invention provides a use of a heterogeneous catalyst in the preparation of a carbapenem, comprising the treatment of a solution of a protected carbapenem with hydrogen gas in the presence of a heterogeneous catalyst to form the carbapenem, wherein the heterogeneous catalyst comprises at least two platinum group metals.

The process conditions described above for the first aspect of the invention generally likewise apply to this aspect of the invention.

Embodiments and/or optional features of the invention have been described above. Any aspect of the invention may be combined with any other aspect of the invention, unless the context demands otherwise. Any of the embodiments or optional features of any aspect may be combined, singly or in combination, with any aspect of the invention, unless the context demands otherwise.

The invention will now be further illustrated by the following Examples, which are for illustrative purposes and as such do not serve to limit the scope of the protection as defined by the claims and with reference to the following Figures in which:

FIG. 1 is a graph illustrating the conversions and selectivities achieved in the synthesis of meropenem with 2.5 wt % $(Pd_xPt_{2.5-x})/C$ catalysts.

FIG. 2 details the results that are obtained utilising nine different Pd,Pt/C catalyst in which the wt % ratio of Pd:Pt are varied (5% total metal), together with the carbon support.

FIGS. 3 and 4 detail the results obtained utilising six different Pd,Pt/C catalyst in which the wt % ratio of Pd:Pt are varied (10% total metal), together with the carbon support. The results for two comparative Pd only catalysts are also provided.

EXAMPLES

Figure 1:
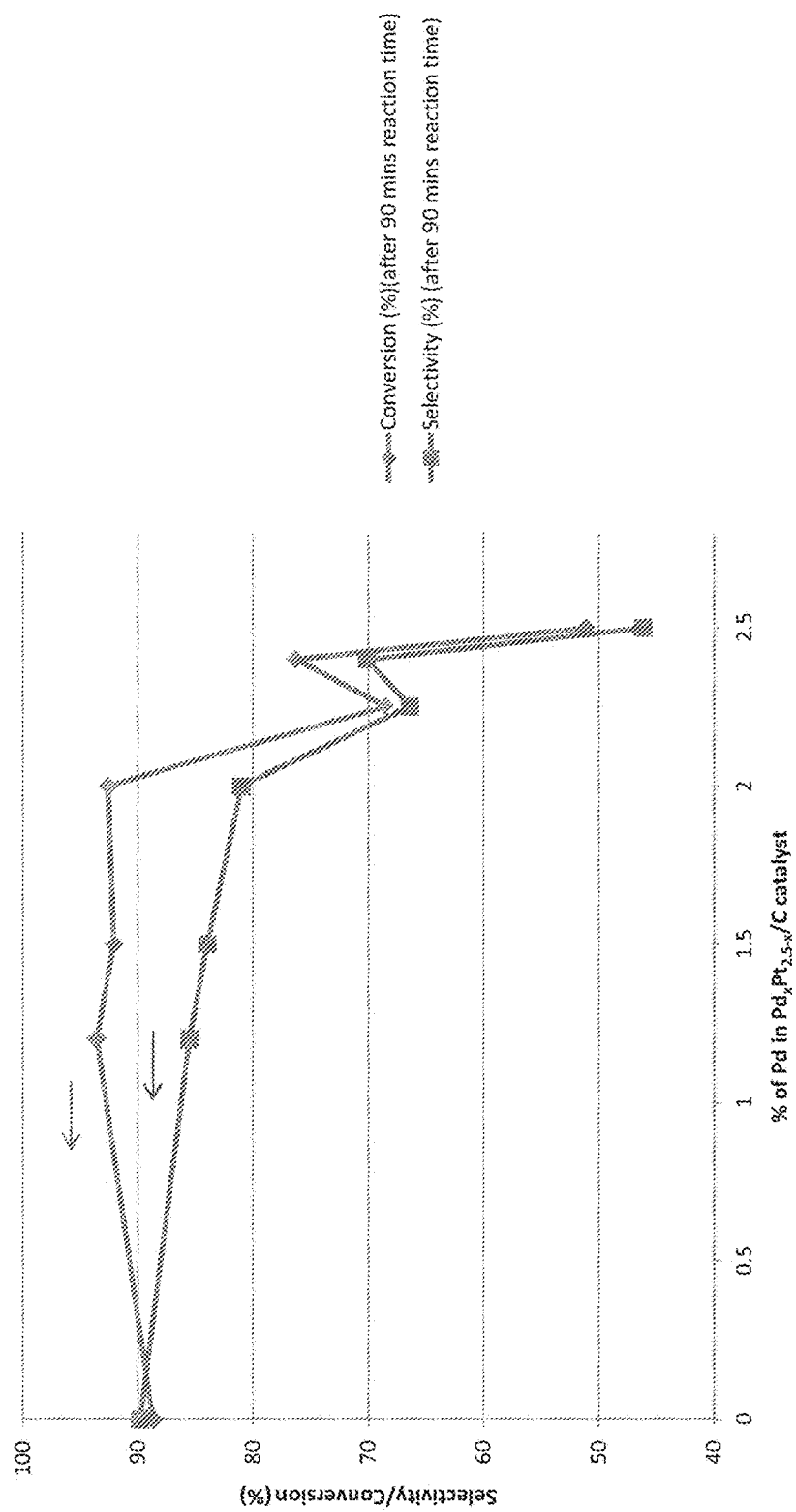

Palladium(II) nitrate solution (having 15.06 wt % Pd by assay), platinum (IV) nitrate solution (having 16.44 wt % Pt by assay), 4-Methylmorpholine (99%), Diisopropylamine (99+%), 1-Methyl-2-pyrrolidinone, anhydrous (99.5%) are obtainable from Alfa Aesar. The carbon support (Ceca ENO, Ceca L4S and Ceca CPL) are commercially available.

The protected meropenem of formula 2 may be prepared according to literature procedure (Sunagawa et al, *Journal of Antibiotics*, 1990, 43, 519-532; U.S. Pat. No. 4,888,344).

HPLC analysis may be carried out according to the procedure described in N. Tewari et al, Organic Process Research & Development 2007, 11, 773-775.

Example 1

Catalyst Preparation

The metal precursor(s) are deposited onto a Ceca ENO activated carbon support by an incipient wetness process.

A 25 ml aqueous solution containing 0.25 g in total of metal by weight is added to 9.75 g of Carbon and this is stirred by hand for one minute so that all of the moisture is taken up. Experiments demonstrate that this is the maximum amount of water that can be added to the activated carbon without observing liquid that is not absorbed.

The solution added varies according to the desired weight loading of the catalyst:

| | Amount of water (ml) | Amount of Platinum(IV) nitrate solution (g) | Amount of Palladium(II) nitrate solution (g) |
|---|---|---|---|
| 2.5 wt % Pd/C* | 25 | 0 | 1.66 |
| 2.4 wt % Pd; 0.1 wt % Pt/C | 25 | 0.06 | 1.59 |
| 2.25 wt % Pd; 0.25 wt % Pt/C | 25 | 0.15 | 1.49 |
| 2.0 wt % Pd; 0.5 wt % Pt/C | 25 | 0.30 | 1.33 |
| 1.25 wt % Pd; 1.25 wt % Pt/C | 25 | 0.76 | 0.83 |
| 2.5 wt % Pt/C* | 25 | 1.52 | 0 |

*not according to the invention

The mixture is then dried in an oven at 105° C. for 24 hours. After this time, 5.0 g of the resulting black powder is transferred to a silica crucible and placed in a Carbolite STF tube furnace and a flow of 5% $H_2/N_2$ of approximately 0.5 L/minute is passed over the sample. After dwelling for ten minutes, the furnace is programmed to heat at a ramp rate of 10° C./minute up to 200° C. It is held at this temperature for one hour before cooling back to room temperature.

Diprotected Meropenem Screening Reactions

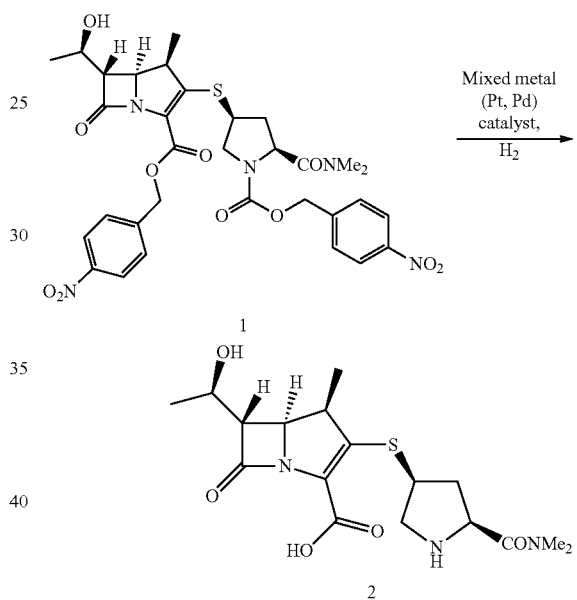

The equipment used for the reaction screening is an HEL Chemscan unit, which has eight individual reaction tubes.

The buffer solution is made as follows. 1.06 g 4-Methylmorpholine+0.43 g g-Acetic acid and made up to 100 ml with water. The buffer is required to be in the pH 7.0-pH 7.5 range. This is achieved by adjusting either component. In this case approximately 20 uL of 4-methylmorpholine is added to bring the pH back up to 7.1.

The catalytic reaction is undertaken using 35 mg of the dry mixed metal catalyst (equating to 25% catalyst loading by weight with respect to the substrate). To this is added 0.140 g of the substrate, 3 ml of ethyl acetate and 2 ml of buffer solution. Prior to the reaction, the vessels are purged 5 times at room temperature (without stirring) with nitrogen and subsequently hydrogen gas. The reaction is then run at 26° C., 6.48 bar of hydrogen, a stirring rate of 900 rpm for 90 minutes. During the reaction, the temperature and pressure values are maintained and the hydrogen uptake is recorded.

The reaction tubes are removed from the Chemscan and the contents of each is separately decanted into individually numbered test tubes. Each reaction tube is washed twice with 5.0 ml of methanol and the washings added to the appropriate numbered test tube. All the test tubes are then sonicated for 15 minutes. Sample filters are made up by taking about 10 cm² of single ply Kimtech Science paper tissue and packing it tightly into a glass Pasteur pipette down to the tip end. Then approximately 1 ml of each sonicated solution is filtered under gravity.

Results

| Amount of Pd in 2.5 wt % $(Pd_xPt_{2.5-x})$/C catalyst | Conversion (%) (after 90 mins reaction time) | Selectivity (%) (after 90 mins reaction time) |
| --- | --- | --- |
| 2.5* | 51.1 | 46.2 |
| 2.4 | 76.4 | 70.1 |
| 2.25 | 68.5 | 66.4 |
| 2 | 92.6 | 81.0 |
| 1.5 | 92.1 | 84.0 |
| 1.25 | 93.6 | 85.5 |
| 0* | 88.7 | 89.8 |

*not according to the invention

The data presented in the table above is illustrated graphically in FIG. 1. From the data it is seen that replacing palladium for platinum in the metal on carbon catalysts results in both an increase in the conversion of the starting material and the selectivity towards the desired product. However, this increase is not linear and it is observed that the yield (i.e. conversion×selectivity) of the desired product is greatest for the mixed-metal materials. For example, the conversion of the mixed metal catalysts that contain 1.25, 1.5, and 2% Pd within the 2.5 wt % $(Pd_xPt_{2.5-x})$/C materials have the highest values. Here, it appears that the metals are synergistically combining to give enhanced performance. Furthermore, the selectivities of the mixed metal catalysts are significantly greater than a weighted average of the two monometallic analogues, again exhibiting synergistic behaviour.

Example 2

The Pd,Pt/C catalysts utilised in this Example may be obtained commercially from Johnson Matthey Catalysis and Chiral Technologies or may be prepared by aqueous slurry impregnation of metal salt components onto an activated carbon support followed by reduction using methods known in the art, for example, as described by G. J. K. Acres et al in "The Design and Preparation of Supported Catalysts", Catalysis Volume 4, pages 1-30, Royal Society of Chemistry, January 1981.

Process Followed for Hydrogenation:

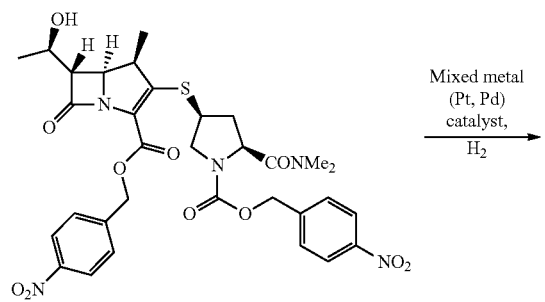

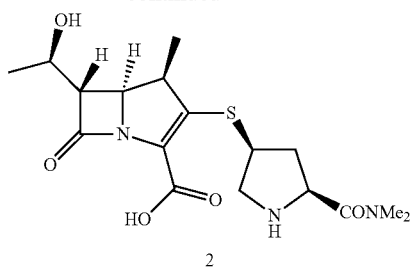

Protected meropenem of formula 1 above (2.5 g), tetrahydrofuran (THF) (63.5 mL), water (50 mL), 2,6-lutidine (0.5 mL) and a Pd,Pt/C paste (30% dry wt basis) (based on the catalysts identified in FIG. 2) are added and the mixture is hydrogenated at 260 psi for 70 minutes and 40° C. At the end of the reaction, the $H_2$ pressure is released and the mass is filtered over celite bed. The catalyst bed is washed with minimum amount of water (10 mL).

Isolation of Product from Solution:

The obtained filtrate is cooled in ice (0-2° C.) and meropenem of formula 2 above is crystallized out by the drop wise addition of pre-cooled acetone (188.5 mL) over 1 hour. Meropenem precipitates out as a solid. The solution containing meropenem is allowed to stir at 0-2° C. for a further 30 minutes and is filtered, washed with a cooled mixture of acetone (12.5 mL) and water (4 mL). The product is dried under vacuum for 30 minutes.

Purification of Crude Meropenem:

The product is dissolved in THF-water mixture (1.3:1) by warming to 40° C. and is filtered. The filtrate is cooled and the product is crystallized by addition of acetone. The solid obtained is dried under vacuum.

Results

FIG. 2 details the results that are obtained utilising nine different Pd,Pt/C catalyst in which the wt % ratio of Pd:Pt are varied (5% total metal), together with the carbon support. The conversions are high in all cases, as well as the yields and HPLC purities of the isolated meropenem. The mixed metal catalysts, therefore, demonstrate an increased rate of conversion and/or selectivity resulting in good to excellent isolated yields.

Example 3

The Pd,Pt/C catalysts utilised in this Example may be obtained commercially from Johnson Matthey Catalysis and Chiral Technologies or may be prepared by aqueous slurry impregnation of metal salt components onto an activated carbon support followed by reduction using methods known in the art, for example, as described by G. J. K. Acres et al in "The Design and Preparation of Supported Catalysts", Catalysis Volume 4, pages 1-30, Royal Society of Chemistry, January 1981.

Process Followed for Hydrogenation:

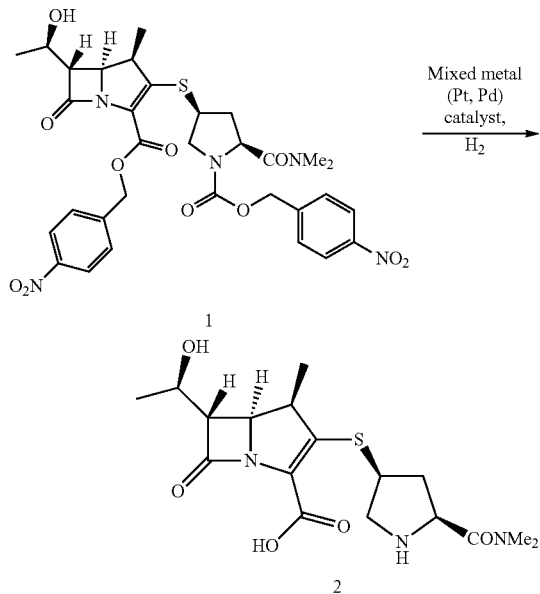

Protected meropenem of formula 1 above (2.5 g), tetrahydrofuran (THF) (63.5 mL), water (50 mL), 2,6-lutidine (0.5 mL) and a Pd,Pt/C paste (50% dry wt basis) (based on the catalysts identified in FIGS. 3 and 4) are added and the mixture is hydrogenated at 150 psi for 120 minutes and 30° C. At the end of the reaction, the $H_2$ pressure is released and the mass is filtered over celite bed. The catalyst bed is washed with minimum amount of water (10 mL).

Isolation of Product from Solution:

The obtained filtrate is cooled in ice (0-2° C.) and meropenem of formula 2 above is crystallized out by the drop wise addition of pre-cooled acetone (188.5 mL) over 1 hour. Meropenem precipitates out as a solid. The solution containing meropenem is allowed to stir at 0-2° C. for a further 30 minutes and is filtered, washed with a cooled mixture of acetone (12.5 mL) and water (4 mL). The product is dried under vacuum for 60 minutes and under vacuum with a $N_2$ purge for 30 minutes.

Results

Figure 5:
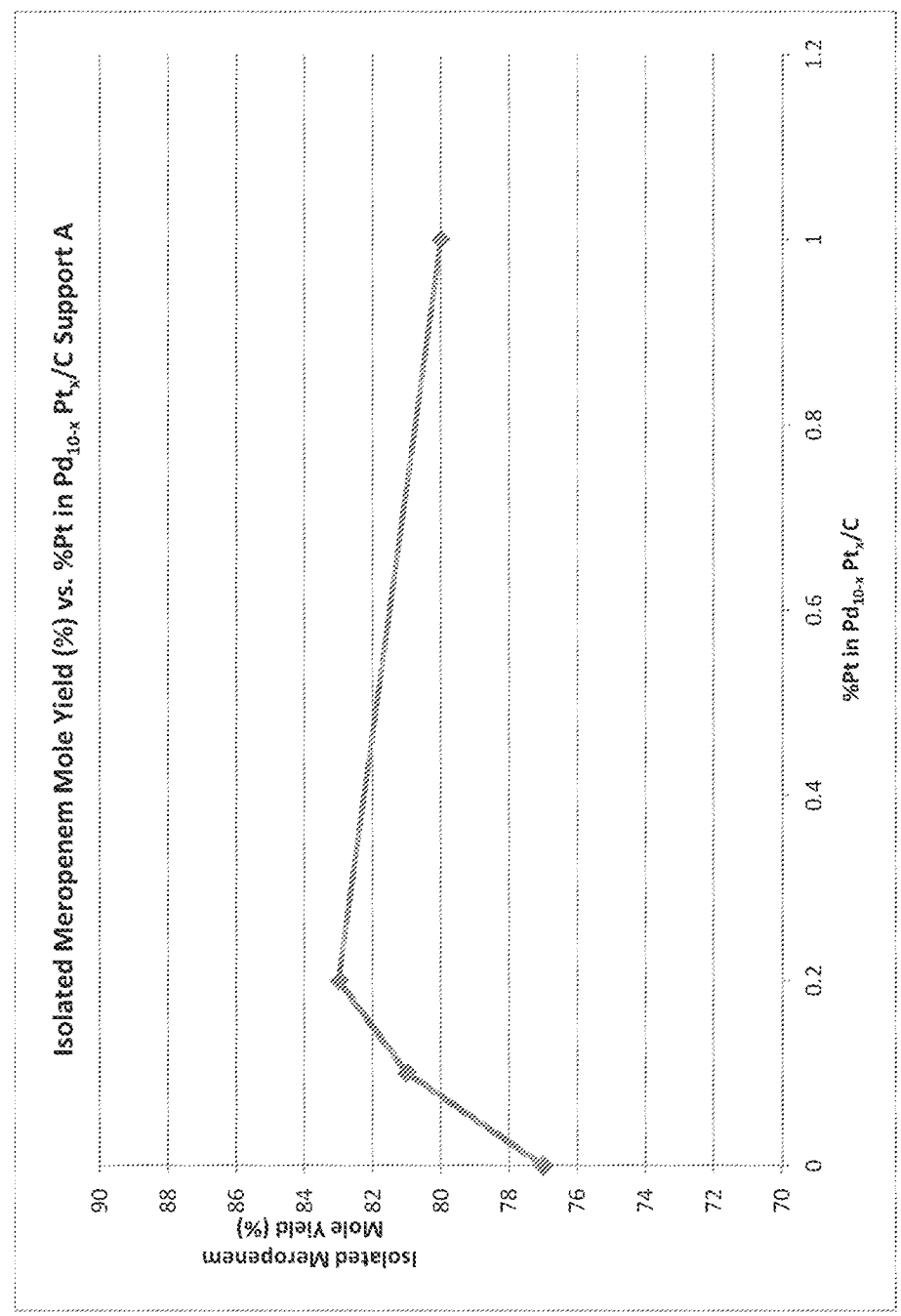
FIG. 5 illustrates the isolated meropenem mole yield (%) vs. % Pt in $Pd_{10-x}Pt_x/C$ catalysts where the carbon support is Ceca L4S.
Figure 6:
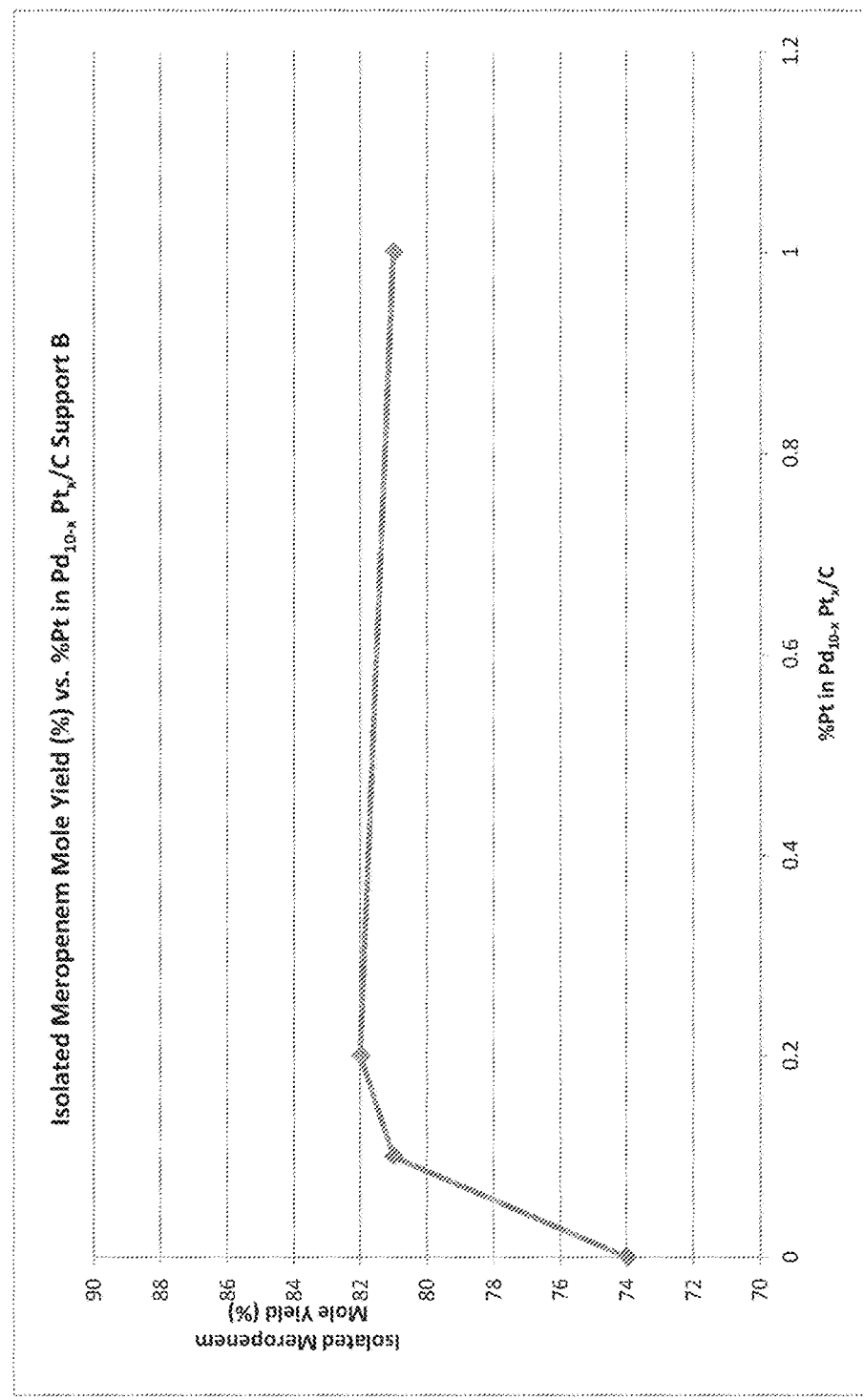
FIG. 6 illustrates the isolated meropenem mole yield (%) vs. % Pt in $Pd_{10-x}Pt_x/C$ catalysts where the carbon support is Ceca ENO.

FIGS. 3 and 4 detail the results obtained utilising six different Pd,Pt/C catalyst in which the wt % ratio of Pd:Pt are varied (10% total metal), together with the carbon support. The results for two comparative Pd only catalysts are also provided. FIGS. 5 and 6 illustrate the isolated meropenem mole yield (%) vs. % Pt in $Pd_{10-x}Pt_x/C$ catalysts where the carbon support is Ceca L4S (FIG. 5) or Ceca ENO (FIG. 6). The conversions are high in all cases, as well as the yields and HPLC purities of the isolated meropenem. However, the mixed metal catalysts give higher isolated meropenem product yields than the Pd only catalysts.

The invention claimed is:

1. A process for preparing a carbapenem that is meropenem, imipenem, ertapenem, thienamycin, panipenem, or doripenem, said process comprising the step of treating a solution of a protected carbapenem with hydrogen gas in the presence of a heterogeneous catalyst to form the carbapenem,
   wherein the protected carbapenem is protected meropenem, protected imipenem, protected ertapenem, protected thienamycin, protected panipenem, or protected doripenem, and the protected carbapenem comprises one or more protecting groups that are an unsubstituted benzyl, substituted benzyl, unsubstituted-carboxybenzyl, substituted-carboxybenzyl, or a combination thereof, and
   wherein the heterogeneous catalyst is a mixed metal catalyst that (a) is an alloy of the two or more platinum group metals; or (b) comprises at least two platinum group metals deposited on a single solid support.

2. A process according to claim 1, wherein the heterogeneous catalyst comprises at least two platinum group metals deposited on a single solid support.

3. A process according to claim 2, wherein the single solid support is carbon, alumina, calcium carbonate, barium carbonate, barium sulfate, titania, silica, zirconia, ceria, or a combination thereof.

4. A process according to claim 2, wherein the single solid support is activated carbon, carbon black, or graphite.

5. A process according to claim 1, wherein the at least two platinum group metals are two or more of ruthenium, rhodium, palladium, iridium, or platinum.

6. A process according to claim 5, wherein the at least two platinum group metals are palladium and platinum.

7. A process according to claim 1, wherein the solution comprises a solvent that is water, a protic solvent, an aprotic solvent, or a mixture thereof.

8. A process according to claim 7, wherein the solvent is water, an alcohol solvent, an ether solvent, an ester solvent, a chlorinated solvent, an amide solvent, or a mixture thereof.

9. A process according to claim 7, wherein the solvent is water, methanol, ethanol, a propanol, a butanol, a pentanol, a hexanol, tetrahydrofuran, 2-methyltetrahydrofuran, dioxane, ethyl acetate, methyl acetate, dichloromethane, dimethylformamide, dimethylacetamide, or mixtures thereof.

10. A process according to claim 1, wherein the process further comprises a base.

11. A process according to claim 10, wherein the base is an inorganic or organic base.

12. A process according to claim 11, wherein the organic base is lutidine.

13. A process according to claim 1, wherein the protected carbapenem comprises one or more protecting groups that are unsubstituted benzyl, unsubstituted carboxybenzyl, or a combination thereof.

14. A process according to claim 8, wherein the solvent is water, methanol, ethanol, a propanol, a butanol, a pentanol, a hexanol, tetrahydrofuran, 2-methyltetrahydrofuran, dioxane, ethyl acetate, methyl acetate, dimethylformamide, dimethylacetamide, or a mixture thereof.

15. A process according to claim 1, wherein the mixed metal catalyst is an alloy of the two or more platinum group metals.

* * * * *